United States Patent [19]
Lewis et al.

[11] Patent Number: 6,121,595
[45] Date of Patent: Sep. 19, 2000

[54] APPLICATOR TO PROVIDE UNIFORM ELECTRIC AND MAGNETIC FIELDS OVER A LARGE AREA AND FOR CONTINUOUS PROCESSING

[75] Inventors: David Andrew Lewis, Carmel, N.Y.; Alfred Viehbeck, Austin, Tex.; Stanley Joseph Whitehair, Peekskill, N.Y.

[73] Assignee: International Business Machines Corporation, Armonk, N.Y.

[21] Appl. No.: 09/002,714

[22] Filed: Jan. 5, 1998

Related U.S. Application Data

[60] Provisional application No. 60/034,717, Jan. 6, 1997.

[51] Int. Cl.⁷ .................................................. H05B 6/70
[52] U.S. Cl. ...................... 219/695; 219/690; 219/693; 219/696; 219/750
[58] Field of Search .................................. 219/690–701, 219/745, 750

[56] References Cited

U.S. PATENT DOCUMENTS

| | | | |
|---|---|---|---|
| 3,461,261 | 8/1969 | Lewis et al. | 219/696 |
| 3,784,777 | 1/1974 | Soulier | 219/690 |
| 4,507,588 | 3/1985 | Asmussen et al. | . |
| 4,585,668 | 4/1986 | Asmussen et al. | . |
| 4,630,566 | 12/1986 | Asmussen et al. | . |
| 4,727,293 | 2/1988 | Asmussen et al. | . |
| 4,760,230 | 7/1988 | Hassler | 219/690 |
| 4,771,153 | 9/1988 | Fukushima et al. | 219/690 |
| 4,777,336 | 10/1988 | Asmussen et al. | . |
| 4,792,772 | 12/1988 | Asmussen et al. | . |
| 5,471,037 | 11/1995 | Goethel et al. | 219/750 |
| 5,869,817 | 2/1999 | Zietlow et al. | 219/696 |

*Primary Examiner*—Tu Ba Hoang
*Attorney, Agent, or Firm*—Ohlandt, Greeley, Ruggiero & Perle

[57] ABSTRACT

A microwave applicator that provides a substantially uniform microwave field distribution over a large area, includes an elongated chamber, preferably operating in the length independent mode. A microwave source generates a microwave field at an output frequency. A waveguide or coaxial cable directs the microwave field from the microwave source into the elongated chamber, either through a side launch, end launch or multi launch. A frequency of the microwave field in the elongated chamber and the output frequency of the microwave source are matched through the use of controlled feedback of critical material and process parameters.

32 Claims, 7 Drawing Sheets

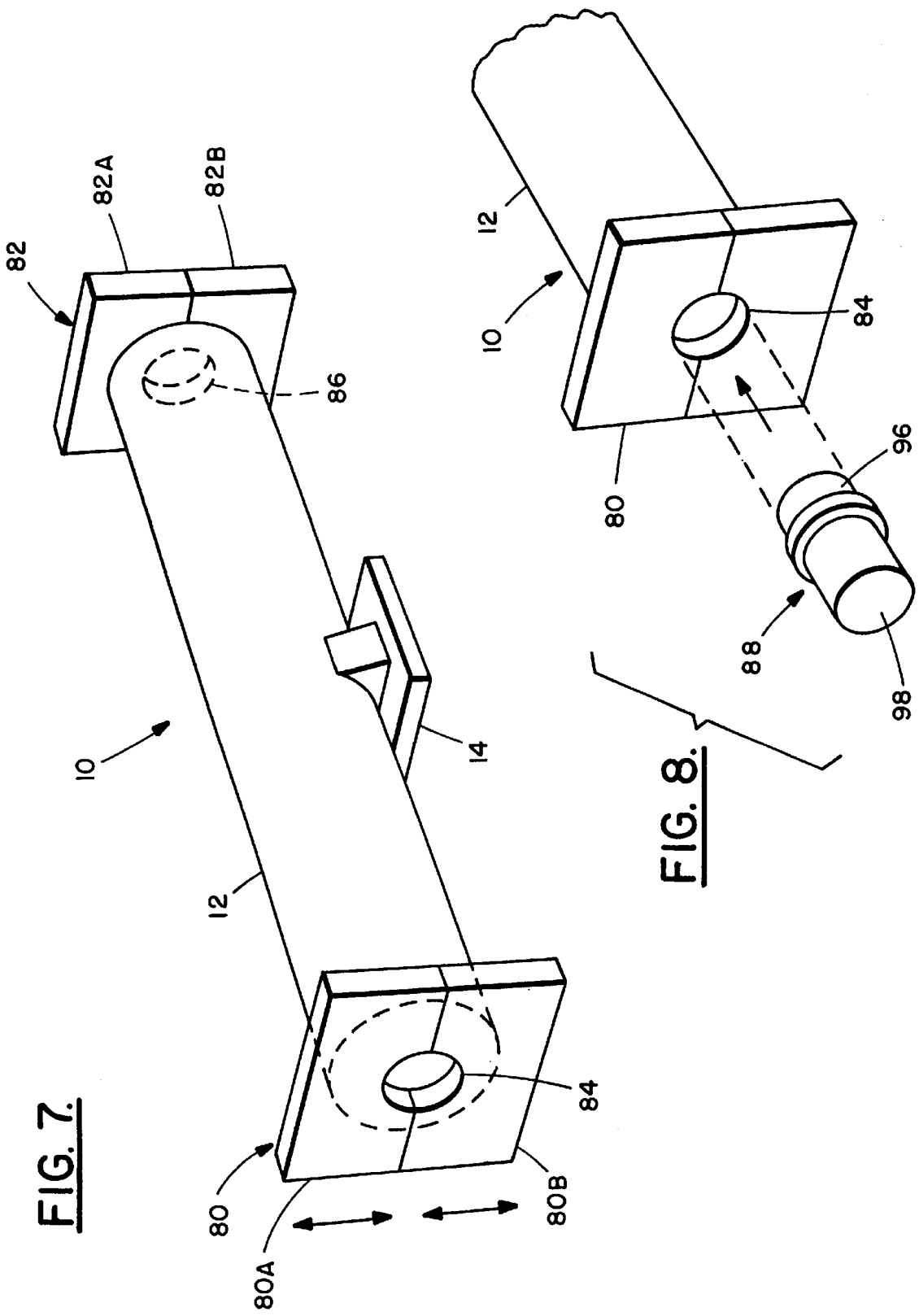

APPLICATOR TO PROVIDE UNIFORM ELECTRIC AND MAGNETIC FIELDS OVER A LARGE AREA AND FOR CONTINUOUS PROCESSING

This application claims the priority from U.S. Provisional Application Ser. No. 60/034,717 filed Jan. 6, 1997.

FIELD OF THE INVENTION

The present invention relates to microwave applicators and, more particularly, to a microwave applicator that can provide uniform electric and magnetic fields over a large area.

BACKGROUND OF THE INVENTION

Microwave radiation can be applied to a material in a number of ways, using single mode, multimode applicators, traveling wave applicators, slow wave applicators, fringing field applicators and through free space. Each of the aforementioned methods of coupling microwave energy into a material has its advantages and disadvantages which usually depend on the dielectric properties, size and shape, of the materials to be processed and the type of processing (batch, continuous, . . . etc.) to be performed.

Efficient microwave energy transfer is a function of many variables as processing occurs. A number of these variables are material related, e.g., the material type and density and material temperature as well as the time history of both the material temperature and the applied electric field. As the material is heated, the dielectric constant may exhibit hysteresis in temperature and electric field strength. Depending on the nature of the change of the dielectric constant, this may result in the application of a non-uniform electric field or thermal runaway, e.g., hot and cold spots within the material.

Other factors that influence coupling are related to the applicator, material geometry and size and the frequency or wavelength of the electromagnetic energy. Electromagnetic coupling depends on applicator size and geometry, material size and shape, the position of the material within the applicator, and even the relative sizes and shapes of the material and the applicator. In addition, both the applicator and material dimensions may change during heating which further complicates the efficient transfer of energy to the material.

Accordingly, a problem arises when attempting to generate a uniform microwave field across a relatively large surface for different material loads. As generally understood, if the volume of an applicator becomes too large, more than one electric field pattern can co-exist in the applicator, thereby making it multimode and introducing electric field non-uniformities. Current microwave applicators are incapable of generating a uniform microwave field across a surface that is relatively large compared to the wavelength of the radiation.

For instance, traveling wave applicators have some potential for providing uniformity. However, stray reflections, such as those that occur at the edges of a workpiece or any non-uniformity in the structure of the applicator can create standing waves leading to thermal non-uniformities. This is especially problematic in cases in which the material travels through more than one applicator and the dielectric properties of the material change depending on the processing conditions in the previous applicator.

An applicator design which shows some promise for applying uniform fields is a single mode applicator, provided that the fields can be extended over a sufficiently large region. This type of applicator can be tuned to specific electric field patterns (resonance modes) by varying the volume of the applicator.

One such approach is found in U.S. Pat. Nos. 4,507,588, 4,585,668, 4,630,566, 4,727,293, and 4,792,772 (Asmussen), all of which disclose methods and apparatuses in which a single mode resonant microwave applicator can be critically coupled by varying two separate, almost orthogonal variables, specifically the cavity length (by moving a short circuit) and the antenna position.

The Asmussen devices include a variable penetration antenna structure which acts to launch radiation into the applicator. The main advantage of the Asmussen device is that it enables complete critical coupling over a wide range of impedances (generated by the load in the applicator) and without the use of any external coupling structure. Critical coupling can thus be achieved by moving the short and the antenna appropriately.

By moving the flat part of the cavity wall (in a cylinder) in the z-direction (e.g., along the centerline of the cylinder), a wide range of electromagnetic modes can be established and maintained, even as the load varies (due to processing, e.g., temperature changing, material curing, etc.). However, one series of modes that cannot be routinely excited are length independent modes, $TM_{xy0}$ and $TE_{xy0}$. The resonant frequencies of these modes are only dependent on the diameter of the loaded structure. As a result, if the load changes during processing (e.g., the dielectric properties change, due to increased temperature, curing, phase change in the material and so forth), the resonant frequency in the cavity changes from an initial, fixed processing frequency, usually 2450 MHz or 915 MHz (which are the ISM bands allowed by the Federal Communication Commission (FCC)). The Asmussen devices are thus not capable of maintaining certain modes in a controlled manner, namely the length independent modes ($TM_{xy0}$ and $Te_{xy0}$), because these modes are dependent on the diameter of the applicator.

U.S. Pat. No. 5,471,037 (Goethal) discloses a single mode cylindrical applicator that operates in the $TM_{02n}$ resonant mode. The microwave applicator is designed to process monomers in order to produce prepolymers. The size of the microwave applicator is selected according to the particular monomers being processed (e.g., fixed dimension applicator). Therefore, there is no mechanism for altering the diameter of the applicator to account for substantially different loads or substantially different dielectric properties.

U.S. Pat. No. 3,461,261 (Lewis) relates to a $TM_{02n}$ applicator that processes threads and yarns with the workpieces passing along the central axis of the applicator. The dimensions of the microwave applicator are selected according to the materials being processed (e.g., fixed dimension applicator).

In general, to process wide objects in a continuous manner, such as a web or a sheet like product, as found in the paper industry, lumber industry (plywood) or electronics industry (in pre-impregnated cloth for circuit board manufacture), it is desirable to be able to (i) provide a uniform electric field over the entire product for uniform heating; (ii) vary the applicator to allow for variations in the dielectric properties of a continuously moving workpiece and, thus, vary the coupling of the radiation into the product; and (iii) control the microwave power reaching the product to control the temperature-time profile of the web.

The electric field pattern sustained by the $TM_{0y0}$ series of modes, where y=1, 2 or greater, is oriented along the z-axis of the applicator and is of constant intensity along the entire length of the applicator for an empty cavity. This is an ideal mode for the processing of a web-like material. Referring to FIG. 1 (a mode chart), it can be seen that the $TM_{010}$ mode is independent of the cavity length. Therefore, a low loss, infinitely long applicator is capable of sustaining the same electric field intensity throughout the length.

There is currently no known method to manipulate the dimensions of a microwave applicator, particularly the cross-sectional diameter, to maintain the resonance and achieve uniform heating of the material (load), using length independent modes. It should also be noted that all electromagnetic modes are dependent on a cross-sectional diameter of the microwave applicator (if the applicator is cylindrical or spheroid), and many have an additional dependence on the length of the applicator.

Accordingly, an object of the present invention is to provide a microwave applicator capable of providing an improved uniform electric and magnetic field over a wide area through the use of controlled feedback of critical material and process parameters.

It is a further object of the invention to provide a microwave applicator whereby field interactions with the material being processed are controlled through tuning of the output frequency of the microwave source.

Another object of the invention is to provide a microwave applicator capable of controlling microwave field uniformity and resonant mode tuning during material processing through the use of a controlled feedback of critical material and process parameters.

It is also an object of the present invention to provide a microwave applicator capable of applying a uniform electric and magnetic field across a sheet of material being transported therethrough in a continuous manner.

Another object of the invention is to provide a microwave applicator that provides improved uniformity of electric and magnetic fields along two dimensional space by launching the radiation into the device via more than one input.

A further object of the invention is to provide a microwave applicator capable of controlling and maintaining length independent modes ($TM_{XY0}$ and $TE_{XY0}$ modes)

SUMMARY OF THE INVENTION

A microwave applicator that provides a substantially uniform microwave field distribution over a large area, includes an elongated chamber, preferably operating in the length independent mode. A microwave source generates a microwave field at an output frequency. A waveguide or coaxial cable directs the microwave field from the microwave source into the elongated chamber, either through a side launch, end launch or multi launch. A frequency of the microwave field in the elongated chamber and the output frequency of the microwave source are matched through the use of controlled feedback of critical material and process parameters.

BRIEF DESCRIPTION OF THE DRAWINGS

FIG. 7 illustrates a microwave applicator of FIGS. 2, 3 and 4 for processing materials through and along a longitudinal axis of the applicator.

FIG. 8 illustrates a choke for use with the microwave applicator of FIG. 7 to prevent radiation leakage.

DETAILED DESCRIPTION OF THE INVENTION

Figure 1:
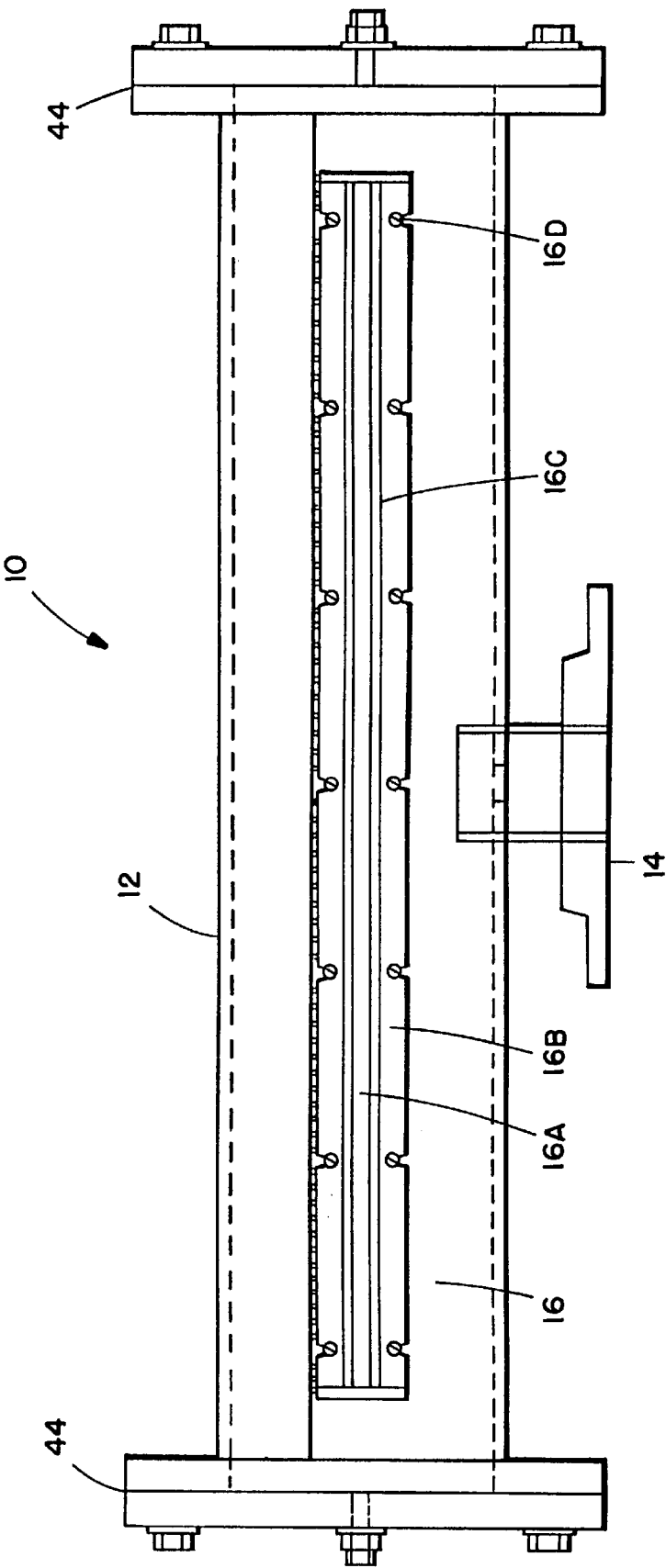
FIG. 1 illustrates a microwave applicator in accordance with the present invention.

Referring to FIG. 1, a microwave applicator 10 in accordance with the present invention includes an elongated chamber 12 for thermally processing a continuous sheet of materials. Elongated chamber 12 preferably has a cylindrical shape, but may be spherical, rectangular, elliptical and so forth. A waveguide 14, coupled to elongated cylinder chamber 12, propagates a microwave field into elongated chamber 12. Microwave applicator 10 is preferably tuned to the $TM_{0n0}$ mode (the length independent mode) in which the electric field is oriented parallel to the axis of the chamber, allowing resonant modes without nodes along the chamber axis can be achieved. By employing the length independent mode, it then becomes possible for microwave applicator 10 to provide microwave energy having a substantially uniform field distribution over a large area for processing materials, for example, a web, in a continuous manner.

In order to control and maintain microwave field uniformity during material processing and to overcome the difficulty in changing effective cavity dimensions, the present invention provides a novel configuration for tuning the resonant frequency of microwave applicator 10 through the use of controlled feedback of critical material and process parameters. The various preferred embodiments will be discussed in detail below.

Figure 2:
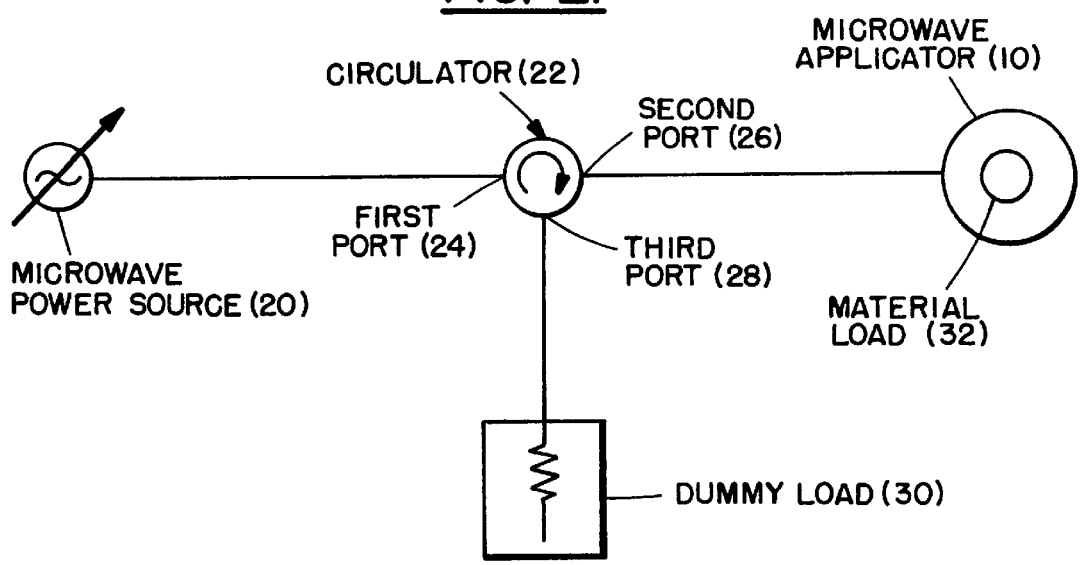
FIG. 2 illustrates a circuit diagram of a first embodiment of the microwave applicator in accordance with the present invention.

Referring to FIG. 2, a first embodiment of the present invention includes a microwave source 20 preferably having a broad bandwidth which is automatically tuned to the frequency of microwave applicator 10 through the use of controlled feedback of critical material and process parameters from the applicator. In particular, critical material and process parameters are fed back to microwave source 20 by reflecting some of the radiation (i.e., reflected radiation) in microwave applicator 10 back into microwave source 20. This has the effect of "pulling" the output frequency of microwave source 20 to match that of the resonance of microwave applicator 10.

It is important to understand that when microwave applicator 10 is critically coupled, the reflected radiation is zero and microwave source 20 is stable. In the event that the output frequency of microwave source 20 starts to drift or the resonant frequency of microwave applicator 10 moves, the reflected radiation in the resonant cavity will increase. In this embodiment, the reflected radiation is utilized as a frequency "lock-in" signal for microwave source 20. This method is very fast, with a time scale of microseconds, but relies upon microwave source 20 having sufficient bandwidth and the exclusion of other resonant frequencies in the range onto which microwave source 20 can lock.

There are currently a number of methods for generating high power microwave energy, such as using a magnetron, klystron, gyrotron, traveling wave tube (TWT) and solid state amplification. Solid state amplification is currently only feasible at 915 MHz and below, and produces relatively low power, with approximately 80 to 100 Watts per stage. Of the aforementioned microwave sources, by far the lowest cost method of generating microwave energy is the cavity magnetron (which is found in all home microwave ovens). Although cavity magnetrons are inexpensive, they have a very narrow spectrum and can only be "pulled" or moved about 10 to 15 MHz. Other types of magnetrons, including coaxial types, have a much greater range over which the output frequency can be pulled, but tend to be more expensive and limited in power output. In this embodiment, it is preferred that microwave source 20 is a magnetron.

As magnetrons can accept relatively large amounts of reflected microwave power without failure, there are a number of ways to provide the "lock-in" signal. The preferred approach is to place a circulator 22 between microwave source 20 (i.e., magnetron) on a first port 24 and a material load 32 on a second port 26 and to generate a mismatch between circulator 22 and a dummy load 30 on a third port 28. An amount of reflected radiation can thus be directed into microwave source 20, via first port 24. This can also be accomplished in a number of ways, such as by utilizing an iris in the waveguide structure, a stub (such as normally found in a stub tuner, but "tuned" to a mismatch position) or some other structure in the waveguide which will create a less than perfect impedance match between circulator 22 and dummy load 30. An alternative approach is to attach microwave source 20 directly to microwave applicator 10, without a circulator or isolator for protection.

Figure 3:
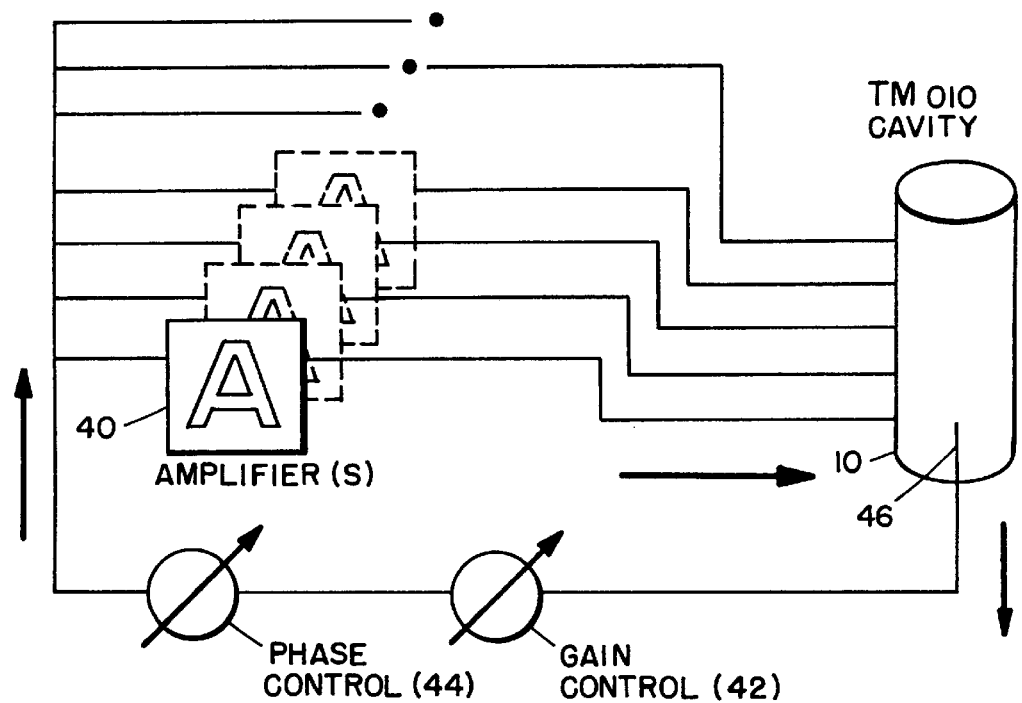
FIG. 3 illustrates a block diagram of a second embodiment of the microwave applicator in accordance with the present invention.

FIG. 3 illustrates a second embodiment of microwave applicator 10 which employs a frequency locking structure to pull the frequency of the microwave source to that of the applicator. To accomplish the foregoing, a plurality of very broad band microwave supplies 40, such as TWT amplifiers or solid state amplifiers, are utilized to match a substantially wider range of resonant frequency loads, ranging from approximately 100 MHz to approximately 300 MHz. It is, however, preferable that microwave supplies 40 have a bandwidth between approximately 400 MHz to approximately 1 GHz. A probe 46, positioned in elongated chamber 12 of microwave applicator 10, transmits a signal containing critical material and process parameters of elongated chamber 12 back to microwave supplies 40, across a gain control module 42 and phase control module 44.

As can be seen, this is accomplished by feeding some of the microwave radiation (i.e., the signal) in elongated chamber 12 initially to gain control module 42 and phase control module 44, via probe 46. Gain control module 42 measures the amplitude of the microwave radiation and ensures that the microwave output of microwave supplies 40 is within a predetermined amplitude range. Thereafter, phase control module 44 measures the frequency (or wavelength) of the microwave radiation and adjusts or tunes the output frequency of microwave supplies 40 to match a frequency of the microwave field in elongated chamber 12. As a result, the output frequency of microwave supplies 40 is "pulled" to that of elongated chamber 12 of microwave applicator 10. It should be noted that these microwave power supplies are very expensive, with high power versions being extremely expensive.

Figure 4:
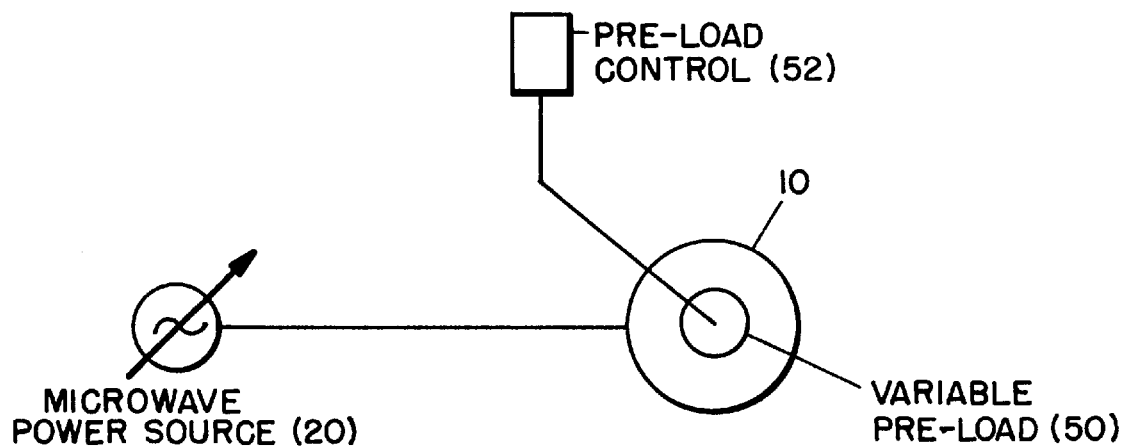
FIG. 4 illustrates a circuit diagram of a third embodiment of the microwave applicator in accordance with the present invention.

Referring to FIG. 4, a third embodiment employs a variable preload 50 in microwave applicator 10 to match the material load, thereby ensuring that substantially all of the microwave energy is coupled into microwave applicator 10 and hence the material load. This is accomplished by preloading elongated chamber 12 with a high dielectric constant material 50 (hereinafter, preload 50). As the material load is introduced into elongated chamber 12, preload 50 is varied (usually reduced) to maintain a resonant frequency for the cylindrical chamber at the output frequency of microwave source 20.

A variable preload 50 can be configured in a number of ways, including the introduction of dielectric rods into the applicator, the use of a bladder containing a high dielectric constant fluid and so forth. During processing, variable preload 50 can be controllably varied by a preload control 52 which receives critical material and process parameters from elongated chamber 12 and adjusts preload 50 to maintain the resonant frequency in the applicator. The preferred forms of variable preload 50 will be discussed in detail below.

In practice, the degree of loading that a dielectric material places on microwave applicator 10 is a function of the dielectric constant of the material load and its position in the microwave field. For instance, if a rod is introduced into a high dielectric region of the microwave field, it will have a greater effect than when introduced into a low dielectric region. If a rod is introduced into a low dielectric region, the mass of the rod must be increased to obtain the same preload 50 as a smaller load in a low dielectric region. Accordingly, by inserting and withdrawing preload 50, in this case preferably a rod or multiple rods, from a position in elongated chamber 12, preload 50 can be varied continuously until the material load becomes greater than the preload and the resonance in microwave applicator 10 can be maintained.

Other bulk matter can also be introduced into microwave applicator 10 to function as variable preload 50 (i.e., an absorber). For example, a non-microwave absorbing elastic material can be used to form an enclosed region, similar to a balloon or bladder, in elongated chamber 12. The elastic material is preferably a rubber such as ethylene-propylene diene monomer (EPDM) or isoprene. A fluid such as silicon oil, can be injected through a hole to inflate the bladder. Likewise, the fluid can be removed by opening a valve and allowing the fluid from the bladder to escape. Such a hydraulic means for adjusting the resonance of microwave applicator 10 is fast and reliable.

For the first, second and third embodiments, microwave radiation can be coupled into microwave applicator 10 using an iris, loop or antenna placed on the outer surface of elongated chamber 12 or from the end of elongated chamber 12 (e.g., end launch). The choice between the aforementioned devices depends on the material to be processed, the manner in which the dielectric properties change during processing and the resonant mode being utilized. Multiple launchers can also be used to improve uniformity and to generate higher power levels in the cavity. They allow the resonant cavity of microwave applicator 10 to act as a power combiner and, at the same time, can be used to minimize any non-uniformities.

Figure 5A:
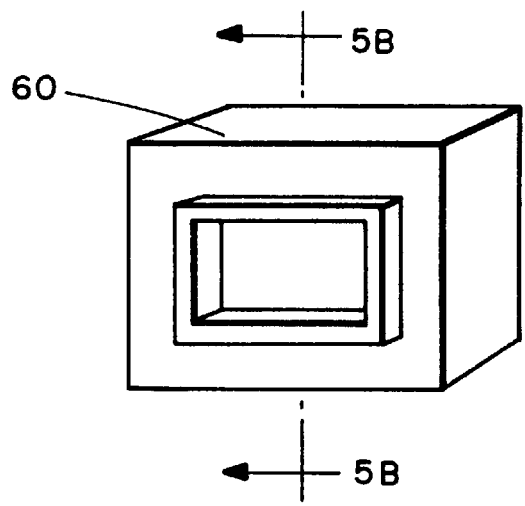
FIGS. 5A and 5B illustrates a top view and cross-sectional view of a preferred aperture.
Figure 5B:
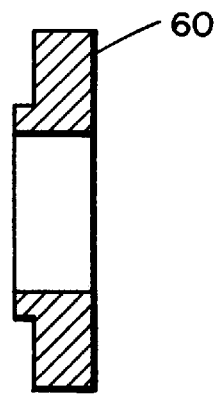
Figure 6:
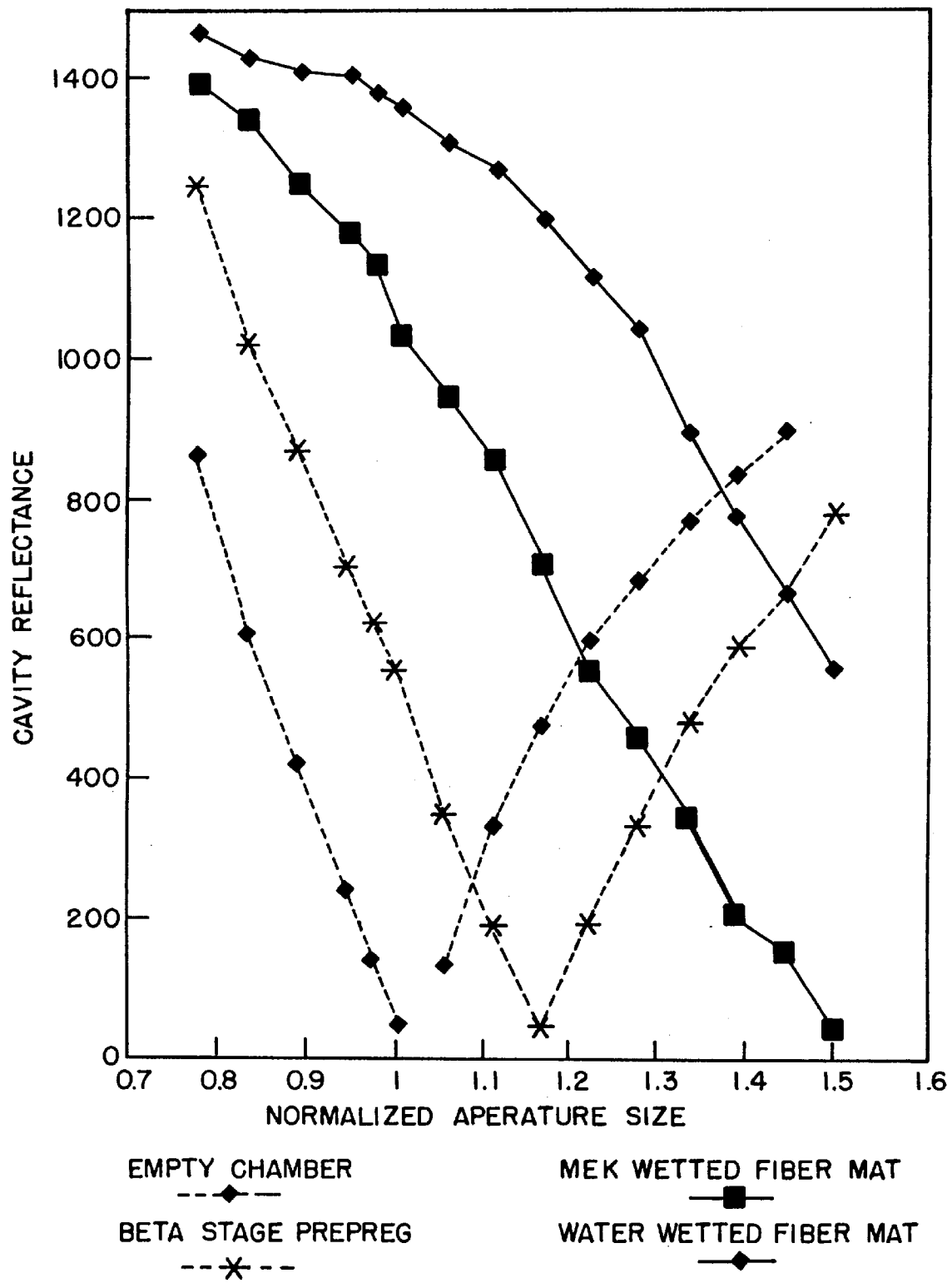
FIG. 6 illustrates a graph explaining the different loads affect on the optimum aperture size.

For cases in which a continuously moving web passes through applicator 10, the dielectric properties of the web reach a steady state after an initial period and change only minimally thereafter. In this case, provided that sufficient microwave energy can be coupled into microwave applicator 10 in the initial period to heat and process the web, only minimal variation in the coupling is required to effectively match the impedance of applicator 10 and obtain substantially complete coupling of the microwave energy into microwave applicator 10. An iris or an aperture (as shown in FIGS. 5A and 5B) can be used. The size of the opening is selected before processing to account for a particular load and, thus, can not be varied during processing. The effect of different loads on the coupling efficiency and aperture size is shown in FIG. 6.

When an iris is placed on the outer wall of the applicator 10 and the fundamental mode of the waveguide is utilized, the length independent $TM_{0n0}$ modes are preferably selected. However, whenever there is a load in microwave applicator 10, mode switching can occur to another mode if the resonant frequency for that mode matches the microwave frequency. This problem is exacerbated as the length of the applicator is increased substantially since the normally length dependent modes can now be selected or sustained.

A continuously variable antenna can also be used to couple microwave energy into the applicator in two modes, e.g., either through a sidewall launch if the TE modes are desired or through an end launch if the TM modes are desired to be excited. Such a device can be constructed in a similar manner to that of U.S. Pat. Nos. 4,507,588, 4,585,668, 4,630,566, 4,727,293, and 4,792,772 (Asmussen). Similarly, a coupling loop (e.g., a magnetic loop) can be utilized in either an end-launch configuration if the TE modes are desired or a side launch configuration if the TM modes are desired.

Turning to practical applications of the present invention, microwave applicator 10 is especially useful for processing thin sheet materials, fabrics, composites, and web structures in a continuous or roll-to-roll format. To accommodate continuous material feed into microwave applicator 10 (FIG. 1), an entrance and exit port or slot is provided in the cylindrical chamber 12. The opening is designed with sufficient clearance to allow the material to pass freely through the orifice without contacting the edges but not too great to perturb the microwave field pattern.

As shown in FIG. 1, elongated chamber 12 preferably includes two product openings 16 extending across the length of the cylinder and positioned on opposing sides of the cylindrical chamber. The material to be processed is inserted through one opening and exits through the other opening. Each opening 16 is preferably defined by a slot 16A, an angle platform 16B and two L-shaped ridges 16C diametrically positioned above and below slot 16A of cylindrical chamber 12. Angle platform 16B and L-shaped ridges 16C extend along the length of opening 16 and are connected to cylindrical chamber 12 by screws 16D. When connected, the above components form an upper and lower ridge having a space therebetween. The material to be processed can be inserted into and out of the cavity of cylindrical chamber 12, via openings 16. It is important to understand that the extending ridges support the material as it is being processed and ensure that the material is fed into microwave applicator 10 along a central horizontal axis.

In the processing of thin sheet polymeric or composite materials, a multiple zone arrangement to control the heating rate and ramp is utilized. For example, in the processing of prepreg, the initial stage involves the removal of solvent (i.e., drying). Subsequently, the resin is advanced to a partial state of cure. In conventional processing, this is accomplished by fixing the temperature of different zones to achieve a particular thermal profile.

Applicator 10, as described above in the first, second and third embodiments, may be employed in various applications for continuous or semi-continuous processing of web or sheet-like materials through a center-feed of elongated chamber 12 (FIG. 1). Examples of such applications include drying paper and textile products (woven and non-woven), curing of coatings, processing of carpet backing and drying and fixing of inks (one color or multi-color). When drying and fixing inks, applicator 10 can be used to process all colors simultaneously or each color individually before a next color is applied. Applicator 10 may also be employed in an application involving both curing and drying, such as the formation of prepreg.

In the above-noted applications, a uniform field over the full width of the web is important and critical. As the weight of the web (fiber density, etc.), the moisture content (entering or exiting) or the thickness of the coating is varied, elongated chamber can be tuned to control uniformity and mode of microwave energy therein during processing of the material.

Applicator 10 is particularly useful over conventional methods for heating of paper-type products, e.g., to dry toner or ink on paper (printed publications) or to remove water from the paper. Conventional heating methods involve the direct application of heat at high temperatures onto the paper, resulting in the thermal degradation of the cellulose of the heated paper. In other words, direct heating of the paper burns and damages the cellulose of the paper. Unlike conventional methods, the present invention couples uniform microwave energy directly to the water, toner or ink (e.g., liquid) on or in the paper and, thus, heats the liquid and not the paper. As a result, there is substantially less degradation of the cellulose in the paper.

Applicator 10 may also be utilized in the formation of a continuous film. Conventionally, the film material is dissolved in a solvent or is carried as a water-based emulsion. The liquid is extruded from a wide opening onto a heated drum where most of the solvent is removed from a very weak but continuous film. Thereafter, the now continuous film is heated to remove the remaining solvent to generate the final properties of the film. However, by utilizing applicator 10, preferably in the $TM_{010}$ mode, it is possible to use microwave energy to remove the solvent with a shorter process length than is possible conventionally. Since the "green strength" of an incompletely processed film is generally extremely poor, applicator 10 of the present invention causes less damage and yield loss than if the film passes over an excessive number of rollers to support the longer process length.

Applicator 10 may also include a conveyor belt (shown in FIG. 9C) passing through the center openings of elongated chamber 12. A semi-continuous or fully continuous feed of materials can be carried by conveyor belt through the internal cavity of elongated chamber 12. Such a system may be utilized for printed circuit boards in order to cure or dry coat solder masks, to die attach adhesives or to underfill (resin applied below a chip to encapsulate the electrical connection), to glob top resins and so forth. Similarly, applicator 10 may be employed in the manufacture of a tape product with a periodic pattern such as TAB (tape automated bonding) tape, which is typically copper patterned structures on a Kapton polymide (manufactured by DuPont™) and optionally with electronic devices or structures attached.

While both the applicators of the first, second and third embodiments have been described above for continuous processing of web or sheet-like materials through a center-feed as shown in FIG. 1, such applicators may also be configured to process materials, such as annular fiber bundles or extrudates, along a substantially central longitudinal axis of the elongated cylinder in a continuous manner. This is accomplished by providing an entry opening in one end support structure (e.g., endplates) of the applicator to allow the materials to be end-fed into the applicator and an exit opening positioned on the other end support structure to allow the processed materials to pass through the applicator. It has been discovered that the cross-sectional diameter of the entry and exit openings can be up to approximately one-half the cross-sectional diameter of the applicator without affecting the performance of the applicator. A more detailed explanation of such end-fed applicator is provided below.

Referring to FIG. 7, an applicator 10 includes an elongated chamber 12 having the cross-sectional area adjusting means of the above first, second and third embodiments shown in FIGS. 1, 2, 3 and 4. Applicator 10 further includes support structures 80, 82 (e.g., endplates) positioned at either ends of elongated chamber 12. Support structure 80 includes an entry opening 84, preferably centrally positioned thereon, for receiving material to be processed. Support structure 82 also includes an opening 86 (hereinafter exit opening), preferably centrally positioned thereon, for allowing materials processed in elongated chamber 12 to exit therethrough. It is preferred that exit opening 86 be aligned with entry opening 84 so that materials to be processed can be continuously fed into and out of elongated chamber 12 along a substantially central longitudinal axis of elongated chamber 12. Openings 84, 86 preferably have an circular-shape, but may have an square, rectangular, oval or elliptical-shape as desired.

In order to accommodate the reception of materials of various sizes and shapes into elongated chamber 12, support structures 80, 82 thereon can be split into two or more movable pieces to enlarge or contract the cross-sectional area of openings 84, 86 respectively. As previously discussed, the cross-sectional diameter of openings 84, 86 can be varied up to approximately one-half the cross-sectional diameter of elongated chamber 12 without affecting the performance of applicator 10. By combining the tuning means of the first, second or third embodiments with the variable end-feed mechanism as described above, various types of materials (having different sizes, shapes and properties) can be fed into elongated chamber 12 by varying the cross-sectional area of entry opening 84 to allow the material to pass therethrough, processed in a uniform manner in elongated chamber 12 by tuning the applicator (as described above in the first, second and third embodiments), and fed out of elongated chamber 12 by varying the cross-sectional area of exit opening 86 to allow the processed material to exit therethrough. The cross-sectional area of openings 84, 86 can either be adjusted before or during processing in accordance with the size and shape of the material to be processed.

It is preferred that support structure 80 is split into two halves 80A, 80B which can be moved towards and away from each other to decrease or increase respectively the cross-sectional area of entry opening 84. As with support structure 80, support structure 82 is preferably split into two halves 82A, 82B and can be moved towards and away from each other to decrease or increase respectively the cross-sectional area of opening 86. It should be noted that good electrical contact can be maintained between elongated chamber 12 and support structures 80, 82 through the use of metal frequencies, metal bands or the like.

Halves 80A, 80B of support structure 80 and halves 82A, 82B of support structure 82 can either be manually adjusted by an operator or automatically adjusted by a computer controlled unit according to the materials being processed. In this way, applicator 10 may be utilized to process materials having various sizes and shapes in a continuous or semi-continuous manner.

However, as the size of openings 84, 86 increases, the amount of radiation leakage from the openings increases. To remedy this problem, applicator 10 may include a choke 88, as shown in FIG. 8, to prevent radiation leakage from entry opening 84. Choke 88 includes an open-ended cavity 98 to allow materials to pass therethrough and an end portion 96 with an exterior mating surface configured to mate with entry opening 84. When end portion 96 of choke 88 is positioned into entry opening 84, the exterior mating surface of choke 88 forms a seal with the interior surface of opening 84 and, thus, prevents leakage of radiation from elongated chamber 12 during processing of the material.

While one choke 88 is shown in FIG. 8 to mate with entry opening 84, there may also be included an additional choke 88 to prevent radiation leakage from exit opening 86. As with entry opening 84, choke 88 can be positioned in exit opening 86 to form a seal therebetween to prevent leakage of radiation, and the materials processed in elongated chamber 12 can exit elongated chamber 12 through the open-ended cavity of choke 88. The length of choke 88 should be a multiple of one fourth (¼) of the wavelength of the radiation length used to process the material.

Figure 9A:
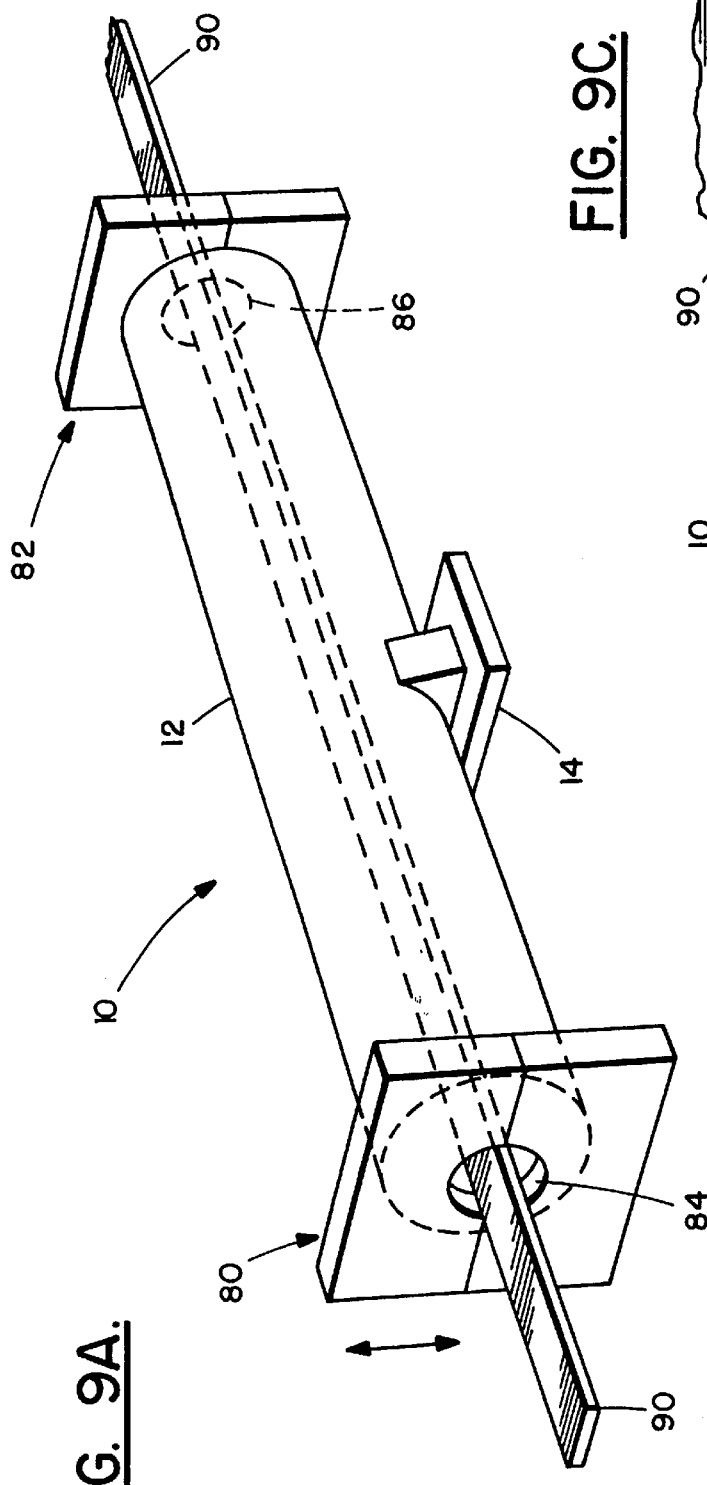
FIG. 9A illustrates a conveyor belt in the microwave applicator of FIG. 7 to provide for continuous processing of materials through the applicator.
Figure 9C:
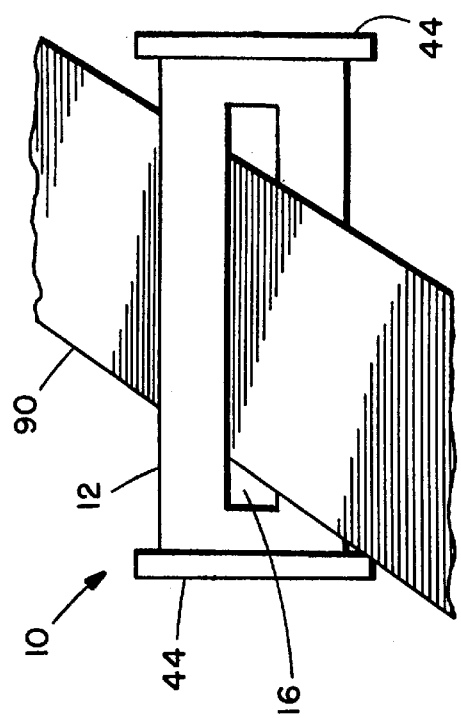
FIG. 9C illustrates a conveyor belt running through a central opening of the microwave applicator of FIG. 1.
Figure 9B:
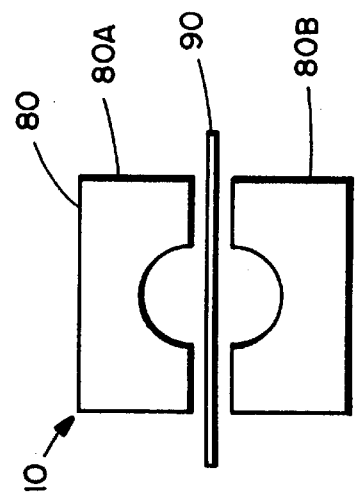
FIG. 9B illustrates a conveyor belt having a cross-sectional width larger than the cross-sectional width of the elongated chamber of the microwave applicator of FIG. 7.

Referring to FIGS. 9A and 9B, applicator 10 may further include a conveyor belt 90 having a portion running between openings 84, 86 along a substantially central longitudinal axis of the chamber. Conveyor belt 90 may be totally contained within the internal cavity of the applicator (FIG. 9A) or extend beyond the cavity walls, via central openings extending along the entire length of elongated chamber 12 (FIG. 9B). Conveyor belt 90 can feed materials through elongated chamber 12 at various processing speeds, in a continuous or semi-continuous manner, depending on the material's properties such as the size, shape, dielectric constant and desired heating period. Conveyor belt 90 provides an easy method for continuously or semi-continuously feeding materials through elongated chamber 12.

Conveyor belt 90 preferably comprises a substantially non-microwave absorbing material (or minimally microwave absorbing material) such as Teflon coated glass fiber or uncoated woven glass fiber; non-woven, non-reinforced Teflon; or polypropylene. Non-reinforced systems may be utilized even though they will not maintain dimensional tolerances.

Figure 10:
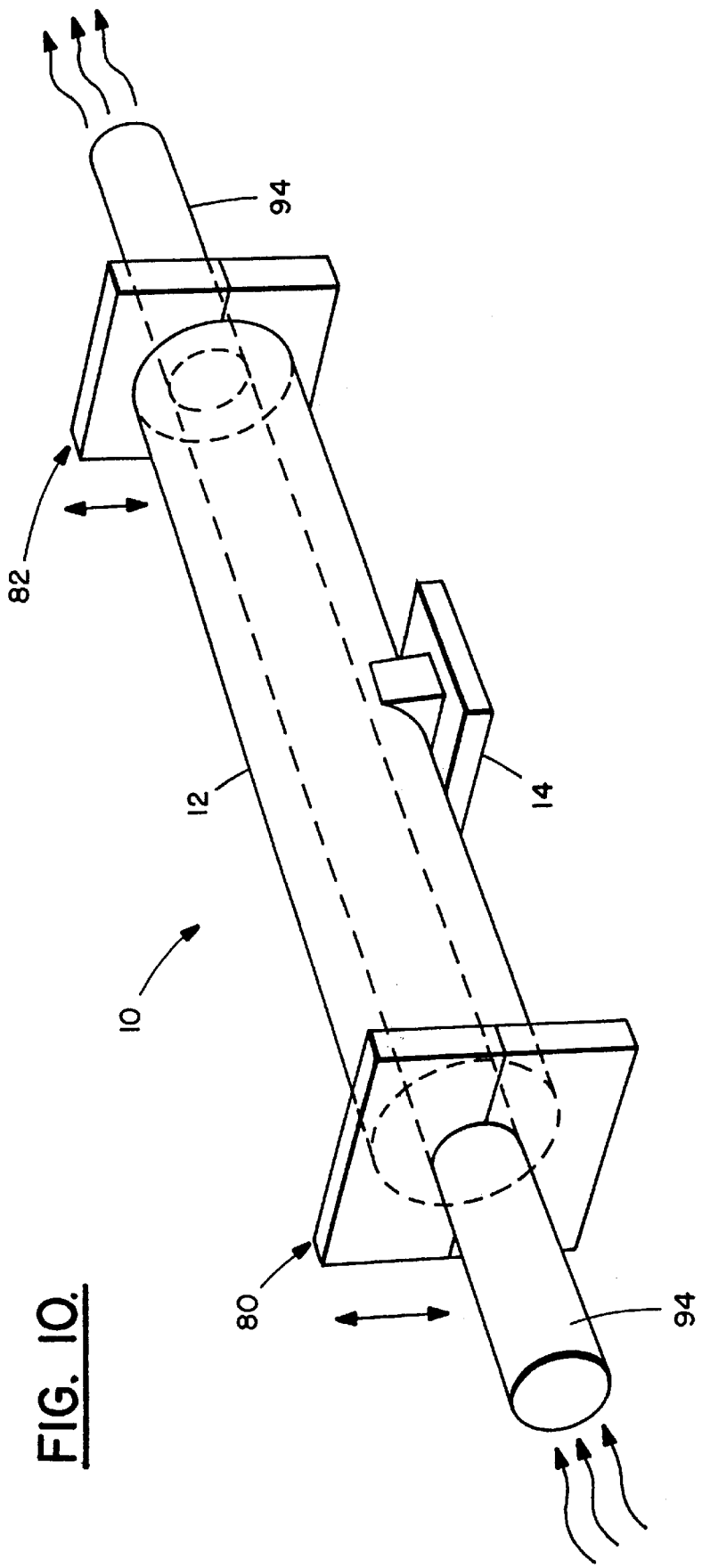
FIG. 10 illustrates a tubular or concentric structure position in the microwave applicator of FIG. 7 to provide for continuous processing of liquid-based materials through the applicator.

Applicator 10 may also be employed to process liquid-based materials or fluids. As shown in FIG. 10, applicator 10 may include a non-metallic tubular or concentric structure 94 running between openings 84, 86 along a substantially central longitudinal axis of elongated chamber 12 (e.g., along the length of elongated chamber 12). A reactant stream of the liquid (to be processed) flows through tubular structure 94 and is processed accordingly. Applicator 10 can thus be employed to heat any material in liquid form, such as organic reactants, to increase or decrease the speed of a chemical reaction. Elongated chamber 12 can be oriented in a vertical or horizontal direction and the reactant flow can also be in any direction.

As can be appreciated by those skilled in the art, such an arrangement provides a cold wall reactor with a heating zone typically in a portion of tubular structure 94 that is central to elongated chamber 12, e.g., where the microwave energy is propagated into elongated chamber 12. Therefore, microwave energy is directly coupled to the reactant stream, while the tubular structure 94 remains unaffected and cool (except possibly for heat conduction by the heated liquid). It is important to understand that a cool wall reactor (e.g., tubular structure 94), as disclosed in the present invention, avoids the heating non-uniformities caused by hot wall reactors such as those found in conventional heating systems. As commonly understood by those skilled in the art, materials processed in contact or proximity with hot walls are subjected to additional heating, thereby resulting in non-uniform heating of the material.

The incorporation of tubular structure 94 also enables corrosive liquids such as acids to be processed therein so as not to damage or corrode the metallic surface of elongated chamber 12. For instance, hydrofluoric acid may be injected into tubular structure 94 and heated to a desired temperature in applicator 10, without damaging the surface of elongated chamber 12.

Although only one applicator 10 has been described above for use in the continuous processing (end-feed or center-feed) of various types of materials, a multiple zone arrangement to control the heating rate and thermal ramp can also be utilized in the processing of thin sheet polymeric or composite materials. For example, in the processing of prepreg, the initial stage involves the removal of solvent (e.g., drying). Subsequently, the resin is advanced to a partial state of cure. In conventional processing, this is accomplished by fixing the temperature of different zones to achieve a particular thermal profile.

In the present invention, a similar thermal profile can be achieved by passing the material being processed through multiple microwave applicators 10 positioned in series, where the material is fed from one microwave applicator to the next. If the dielectric properties of the material load continually change during processing, the resonant frequency of each microwave applicator must be varied to accommodate the property change. This can be accomplished through the cross-sectional area adjusting means described. In the case where the material load goes through significant changes, the structural dimensions of each individual microwave applicator 10 is configured to account for the different property changes. The benefits of such a multi-zone or multi-pass microwave applicator arrangement is that increased process control is attained.

In addition to the continuous processing methods as described above, elongated chamber 12 of the first, second and third embodiments (FIGS. 1, 2, 3 and 4) may also be employed to batch process materials. Either of the two support plates 44 (endplates) of applicator 10 may be configured to be movable to an open and closed position (e.g., hinge coupled) or removable. During the operation of the invention, support structure 44 is moved to an open position or removed to allow loading of elongated chamber 12. After processing, support structure 44 is moved to an open position or removed and the processed material is removed. Note that support structure 44 can be driven by a piston to automate the processing and withdrawn on the same axis as the applicator or can be pivoted around one point, depending on the type of material to be loaded and the type of electrical contact between elongated chamber 12 and support structure 44. The end-plates can also be moved a short distance along the axis of applicator 10 and then rotated. Such an applicator system can be used to heat semiconductor wafers or to cure or anneal coatings of layers.

In summary, the present invention provides a microwave applicator that automatically tunes the output frequency of the microwave source and the frequency of the cylindrical chamber for varying loads by utilizing controlled feedback of critical material and process parameters. As can be appreciated, the resonant frequency in the microwave applicator can be maintained without varying the structural dimensions of the applicator.

The invention having thus been described with particular reference to the preferred forms thereof, it will be obvious that various changes and modifications may be made therein without departing from the spirit and scope of the invention as defined in the appended claims.

What is claimed is:

1. A microwave applicator for providing a substantially uniform microwave energy distribution over a large area, comprising:

an elongated chamber including an entry opening and an exit opening, respectively positioned on opposite sides and along a transverse axis to a long axis of said elongated chamber, for allowing material to pass therethrough along said transverse axis;

a microwave source for generating microwave energy at an output frequency;

means for coupling said microwave energy into said elongated chamber so as to induce therein an electric field oriented parallel to said long axis with a resonant mode that is without nodes along said long axis; and means for matching a resonant frequency of said elongated chamber and said output frequency of said microwave source, in accord with sensed changes in said resonant frequency as affected by a material passing through said elongated chamber.

2. A microwave applicator as recited in claim 1, wherein said entrance and exit openings allow a sheet of material to pass centrally along said transverse axis.

3. The microwave applicator as recited in claim 1, wherein said means for matching includes means, responsive to changes in said resonant frequency to tune said resonant frequency of said elongated chamber to said output frequency.

4. The microwave applicator as recited in claim 1, wherein said output frequency ranges between approximately 100 MHz and approximately 300 GHz.

5. The microwave applicator as recited in claim 1, wherein said accepting means comprises a movable end portion of said elongated chamber.

6. The microwave applicator as recited in claim 1, wherein said means for accepting includes means for adjusting a cross-sectional diameter of said entry opening.

7. The microwave applicator as recited in claim 1, wherein said means for accepting includes means for adjusting a cross-sectional diameter of said exit opening.

8. The microwave applicator as recited in claim 1, further comprising a choke for preventing radiation leakage from said entry opening.

9. The microwave applicator as recited in claim 1 further comprising a choke for preventing radiation leakage from said exit opening.

10. The microwave applicator as recited in claim 1, further comprising means for feeding said material through said elongated chamber.

11. The microwave applicator as recited in claim 10, wherein said means for feeding comprises a conveyor belt having a portion running between said entry opening and said exit opening.

12. The microwave applicator as recited in claim 11, wherein said conveyor belt comprises a substantially non-microwave absorbing material.

13. The microwave applicator as recited in claim 12, wherein said conveyor belt comprises a perfluorinated polymeric material.

14. The microwave applicator as recited in claim 10, further comprising means for holding said material having a liquid form in said elongated chamber, said means for holding having a portion running between said entry opening and said exit opening.

15. The microwave applicator as recited in claim 14, wherein said means for holding allows said material to flow through said elongated chamber along a substantially central longitudinal axis of said elongated chamber.

16. The microwave applicator as recited in claim 14, wherein said means for holding comprises a tubular structure.

17. The microwave applicator as recited in claim 16, wherein said tubular structure comprises a substantially non-microwave absorbing material.

18. The microwave applicator as recited in claim 17, wherein said tubular structure comprises a perfluorinated polymeric material.

19. The microwave applicator as recited in claim 17, wherein said tubular structure comprises quartz.

20. The microwave applicator as recited in claim 1, wherein said elongated chamber has an approximately square cross-section.

21. The microwave applicator as recited in claim 1, wherein said elongated chamber has an approximately rectangular cross-section.

22. The microwave applicator as recited in claim 1, wherein said elongated chamber has an approximately elliptical cross-section.

23. The microwave applicator as recited in claim 1, wherein said elongated chamber has an approximately circular cross-section.

24. The microwave applicator as recited in claim 1, wherein said means for matching includes means for directing an amount of reflected radiation from said elongated chamber to said microwave source.

25. The microwave applicator as recited in claim 24, wherein said means for directing includes a circulator, coupled between said microwave source and said elongated chamber.

26. The microwave applicator as recited in claim 1, wherein said microwave source is directly coupled to said elongated chamber.

27. The microwave applicator as recited in claim 1, wherein said means for matching includes variable preload means capable of being varied such that said frequency in said elongated chamber matches said output frequency of said microwave source.

28. The microwave applicator as recited in claim 27, wherein said variable preload means includes at least one rod having a predetermined dielectric property, said rod being selectively inserted into or removed from said elongated chamber.

29. The microwave applicator as recited in claim 27, wherein said variable preload means includes means, maintained in said elongated chamber, for holding a variable amount of liquid, said amount of liquid being selectively varied to match said frequency of said elongated chamber to said output frequency.

30. The microwave applicator as recited in claim 29, wherein said holding means includes hydraulic means for controlling liquid flow in and out of said holding means.

31. The microwave applicator as recited in claim 29, wherein said holding means is made of rubber.

32. A microwave applicator as recited in claim 1, wherein said mode is a $TM_{0Y0}$ mode, where Y is an integer >0.

* * * * *